United States Patent
Cohen et al.

(10) Patent No.: US 6,764,687 B1
(45) Date of Patent: Jul. 20, 2004

(54) LIVE ATTENUATED BACTERIA FOR USE IN A VACCINE

(75) Inventors: Paul S. Cohen, Narragansett, RI (US); David C. Laux, Narragansett, RI (US); Petrus J. M. Nuijten, Boxmeer (NL)

(73) Assignees: Akzo Nobel N.V., Arnhem (NL); Board of Governors for Higher Education, State of Rhode Island, Providence, RI (US)

( * ) Notice: Subject to any disclaimer, the term of this patent is extended or adjusted under 35 U.S.C. 154(b) by 0 days.

(21) Appl. No.: 09/328,859

(22) Filed: Jun. 9, 1999

(51) Int. Cl.[7] .............................................. A61K 39/112
(52) U.S. Cl. ................. 424/258.1; 424/241.1; 424/234.1; 424/200.1; 435/243; 435/252.3
(58) Field of Search ........................... 424/258.1, 241.1, 424/234.1, 200.1; 435/243, 252.3

(56) References Cited

U.S. PATENT DOCUMENTS 6,090,611 A * 7/2000 Covacci et al.

OTHER PUBLICATIONS

Piedra. Vaccine. 1993. 11(7). p. 718. abstract only.*
Allen et al. Infect. Immun. Jun. 2000. 68(6): 3772–3775.*
Curtiss III et al. Infect. Immun. 1987: 3035–3043.*
Ramseier et al., *J. Mol. Biol.*, vol. 234, pp 28–44, 1993.
Saier et al., *J. Bacteriology*, vol. 178, No. 12, pp. 3411–3417, 1996.
Chin et al., *J. Bacteriology*, vol. 169, No. 2, pp. 897–899, 1987.
Jahreis et al., *Mol. Gen. Genet.*, vol. 226, pp. 332–336, 1991.
Utley et al., *FEMS Microbiology Letters*, 163:129–134 (1998).
David P. Franklin, Dissertation entitled "Isolation and Characterization of Mouse Intestinal Mucus Derived Phosphatidylserine That serves as a *Salmonella* Nutrient: Its Role in Pathogenesis and the Competitive Colonization of the Stretomycin–Treated Mouse", Univ Rhode Island (1992).

* cited by examiner

*Primary Examiner*—Jennifer E. Graser
(74) *Attorney, Agent, or Firm*—William M. Blackstone

(57) ABSTRACT

The present invention relates to live attenuated bacteria for use as a medicament. The invention also relates to vaccines based thereon that are useful for the prevention of microbial pathogenesis. Further, the invention relates to live attenuated recombinant bacteria carrying a heterologous gene and vaccines based thereon. Finally, the invention relates to methods for the preparation of such vaccines and bacteria.

22 Claims, 4 Drawing Sheets

```
                        SEQUENCE LISTING

<160> NUMBER OF SEQ ID NOS: 2

<210> SEQ ID NO 1
<211> LENGTH: 1200
<212> TYPE: DNA
<213> ORGANISM: Salmonella typhimurium
<220> FEATURE:
<221> NAME/KEY: CDS
<222> LOCATION: (118)..(1119)
<220> FEATURE:
<221> NAME/KEY: misc_feature
<222> LOCATION: (118)..(120)
<223> OTHER INFORMATION: /product="codes for the amino acid methionine"

<400> SEQUENCE: 1
gtggtaaccc ggaataaaag cggttgccgg agtgatcaaa ctgcgcttag atgttaacga     60
ttttaaccca tgccgacata aaggttatgg tttgtacaat ttacacaagg ggcaatt       117 gtg aaa ctg gat gaa atc gct cgg ctg gcc ggt gtc tcg cgc aca act      165
Val Lys Leu Asp Glu Ile Ala Arg Leu Ala Gly Val Ser Arg Thr Thr
  1               5                  10                  15 gca agc tac gtt ata aac ggt aaa gca aag caa tac cgc gtg agc gac      213
Ala Ser Tyr Val Ile Asn Gly Lys Ala Lys Gln Tyr Arg Val Ser Asp
             20                  25                  30 aaa acc gta gaa aaa gtc atg gcg gta gtg cgt gag cac aat tac cat      261
Lys Thr Val Glu Lys Val Met Ala Val Val Arg Glu His Asn Tyr His
         35                  40                  45 cct aac gct gtg gct gcc ggg ctg cgt gct gga cgc aca cgt tcc att      309
Pro Asn Ala Val Ala Ala Gly Leu Arg Ala Gly Arg Thr Arg Ser Ile
     50                  55                  60 ggt ctg gtg atc ccg gac ctt gaa aac acg agc tac acc cgt atc gca      357
Gly Leu Val Ile Pro Asp Leu Glu Asn Thr Ser Tyr Thr Arg Ile Ala
 65                  70                  75                  80 aac tat ctt gag cgc cag gca cgc cag cgt ggc tac caa ctg ctg atc      405
Asn Tyr Leu Glu Arg Gln Ala Arg Gln Arg Gly Tyr Gln Leu Leu Ile
                 85                  90                  95 gcc tgt tct gaa gat cag ccg gat aac gaa atg cgc tgc att gag cac      453
Ala Cys Ser Glu Asp Gln Pro Asp Asn Glu Met Arg Cys Ile Glu His
            100                 105                 110
```

-continued

```
ctt ttg caa cgc cag gtg gat gca atc att gtt tca act tcg tta ccg       501
Leu Leu Gln Arg Gln Val Asp Ala Ile Ile Val Ser Thr Ser Leu Pro
        115                 120                 125 ccg gag cat ccc ttc tat cag cgc tgg gcc aac gat ccg ttc ccc atc       549
Pro Glu His Pro Phe Tyr Gln Arg Trp Ala Asn Asp Pro Phe Pro Ile
    130                 135                 140 gtc gcg ctc gac cgc gcg ctg gat cgc gaa cat ttc acc agc gtg gtc       597
Val Ala Leu Asp Arg Ala Leu Asp Arg Glu His Phe Thr Ser Val Val
145                 150                 155                 160 ggc gcc gat cag gat gat gcc gag atg ttg gcg gaa gag ctg cgt aaa       645
Gly Ala Asp Gln Asp Asp Ala Glu Met Leu Ala Glu Glu Leu Arg Lys
                165                 170                 175 ttc ccg gcg gaa acg gtg ctt tat ttg ggc gcg ctg ccg gag ttg tcc       693
Phe Pro Ala Glu Thr Val Leu Tyr Leu Gly Ala Leu Pro Glu Leu Ser
        180                 185                 190 gtc agt ttc ctg cgc gag cag ggg ttc cgc acc gca tgg aaa gac gat       741
Val Ser Phe Leu Arg Glu Gln Gly Phe Arg Thr Ala Trp Lys Asp Asp
            195                 200                 205 ccg cgg gag gtg aat ttc tta tat gcc aac agc tat gag cgc gaa gcc       789
Pro Arg Glu Val Asn Phe Leu Tyr Ala Asn Ser Tyr Glu Arg Glu Ala
210                 215                 220 gcc gcg cag ttg ttt gag aaa tgg ctg gaa acg cat cct atg ccg cag       837
Ala Ala Gln Leu Phe Glu Lys Trp Leu Glu Thr His Pro Met Pro Gln
225                 230                 235                 240 gcg ctc ttt acg aca tcg ttc gcg cta tta cag ggc gtg atg gac gta       885
Ala Leu Phe Thr Thr Ser Phe Ala Leu Leu Gln Gly Val Met Asp Val
                245                 250                 255 acg ctg cgg cgc gat gga aaa ctg cct tcg gat tta gcg att gcg acc       933
Thr Leu Arg Arg Asp Gly Lys Leu Pro Ser Asp Leu Ala Ile Ala Thr
        260                 265                 270 ttc ggc gat cat gag ctg ctg gat ttt ctg caa tgc ccg gta ctg gcg       981
Phe Gly Asp His Glu Leu Leu Asp Phe Leu Gln Cys Pro Val Leu Ala
    275                 280                 285 gtg gcg cag cgt cat cgt gat gtc gcg gaa cgc gtg ctg gag att gtg      1029
Val Ala Gln Arg His Arg Asp Val Ala Glu Arg Val Leu Glu Ile Val
290                 295                 300 ctg gca agt ctt gat gaa ccg cgt aaa ccg aaa ccc ggc tta acg cgt      1077
Leu Ala Ser Leu Asp Glu Pro Arg Lys Pro Lys Pro Gly Leu Thr Arg
305                 310                 315                 320 att cgg cga aac ctt tat cgt cgc ggc att ctg agc cgt agc                1119
Ile Arg Arg Asn Leu Tyr Arg Arg Gly Ile Leu Ser Arg Ser
                325                 330 taaaggaccg gcggtaaaag actctctctt ctgccgccgt caaacaaatg cgtatcagta    1179
aaaatatccc ttaaataatt a                                              1200

<210> SEQ ID NO 2
<211> LENGTH: 334
<212> TYPE: PRT
<213> ORGANISM: Salmonella typhimurium

<400> SEQUENCE: 2

Val Lys Leu Asp Glu Ile Ala Arg Leu Ala Gly Val Ser Arg Thr Thr
  1               5                  10                  15

Ala Ser Tyr Val Ile Asn Gly Lys Ala Lys Gln Tyr Arg Val Ser Asp
                20                  25                  30

Lys Thr Val Glu Lys Val Met Ala Val Val Arg Glu His Asn Tyr His
            35                  40                  45

Pro Asn Ala Val Ala Ala Gly Leu Arg Ala Gly Arg Thr Arg Ser Ile
```

-continued

```
                50                    55                     60
Gly Leu Val Ile Pro Asp Leu Glu Asn Thr Ser Tyr Thr Arg Ile Ala
65                      70                  75                  80

Asn Tyr Leu Glu Arg Gln Ala Arg Gln Arg Gly Tyr Gln Leu Leu Ile
                    85                  90                  95

Ala Cys Ser Glu Asp Gln Pro Asp Asn Glu Met Arg Cys Ile Glu His
                100                 105                 110

Leu Leu Gln Arg Gln Val Asp Ala Ile Ile Val Ser Thr Ser Leu Pro
            115                 120                 125

Pro Glu His Pro Phe Tyr Gln Arg Trp Ala Asn Asp Pro Phe Pro Ile
        130                 135                 140

Val Ala Leu Asp Arg Ala Leu Asp Arg Glu His Phe Thr Ser Val Val
145                 150                 155                 160

Gly Ala Asp Gln Asp Asp Ala Glu Met Leu Ala Glu Glu Leu Arg Lys
                165                 170                 175

Phe Pro Ala Glu Thr Val Leu Tyr Leu Gly Ala Leu Pro Glu Leu Ser
            180                 185                 190

Val Ser Phe Leu Arg Glu Gln Gly Phe Arg Thr Ala Trp Lys Asp Asp
        195                 200                 205

Pro Arg Glu Val Asn Phe Leu Tyr Ala Asn Ser Tyr Glu Arg Glu Ala
    210                 215                 220

Ala Ala Gln Leu Phe Glu Lys Trp Leu Glu Thr His Pro Met Pro Gln
225                 230                 235                 240

Ala Leu Phe Thr Thr Ser Phe Ala Leu Leu Gln Gly Val Met Asp Val
                245                 250                 255

Thr Leu Arg Arg Asp Gly Lys Leu Pro Ser Asp Leu Ala Ile Ala Thr
            260                 265                 270

Phe Gly Asp His Glu Leu Leu Asp Phe Leu Gln Cys Pro Val Leu Ala
        275                 280                 285

Val Ala Gln Arg His Arg Asp Val Ala Glu Arg Val Leu Glu Ile Val
    290                 295                 300

Leu Ala Ser Leu Asp Glu Pro Arg Lys Pro Lys Pro Gly Leu Thr Arg
305                 310                 315                 320

Ile Arg Arg Asn Leu Tyr Arg Arg Gly Ile Leu Ser Arg Ser
                325                 330
```

LIVE ATTENUATED BACTERIA FOR USE IN A VACCINE

FIELD OF THE INVENTION

Figure 1:
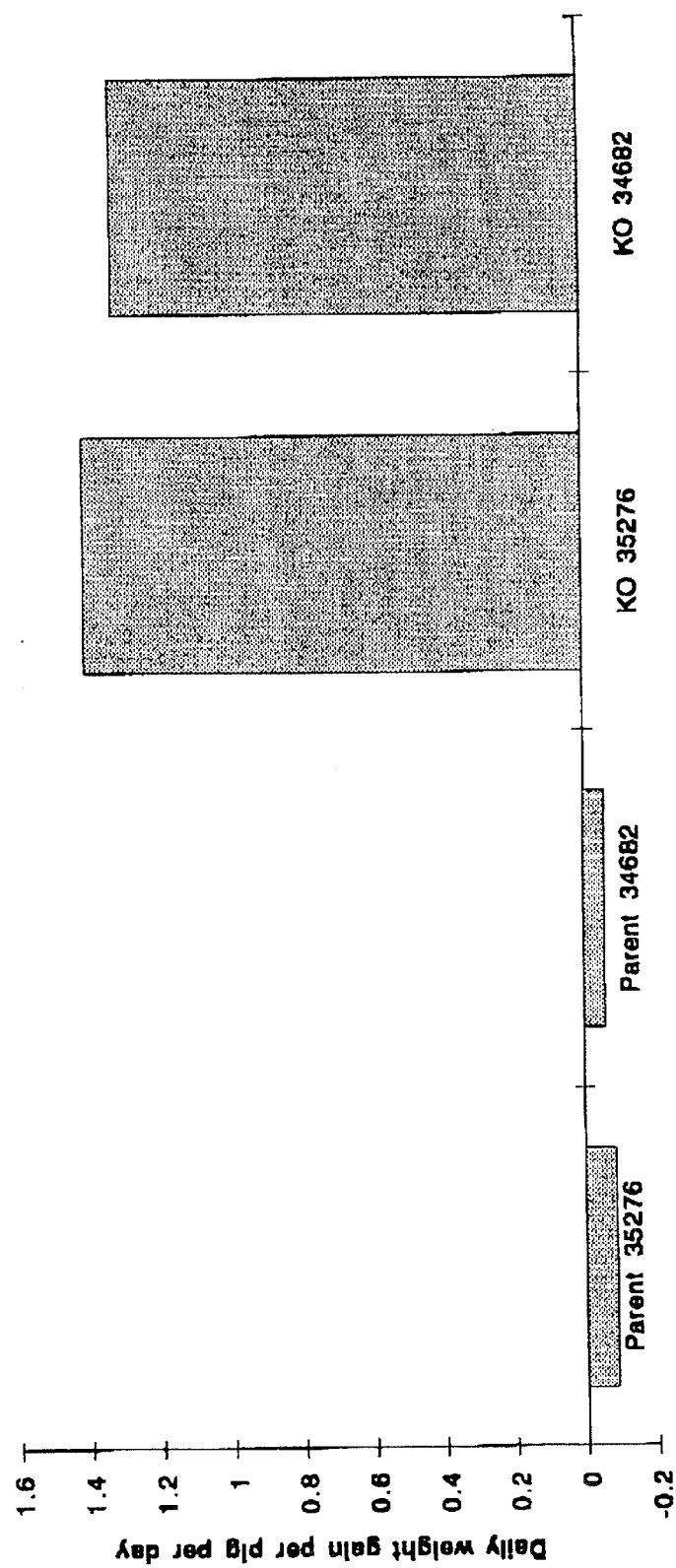
Figure 2:
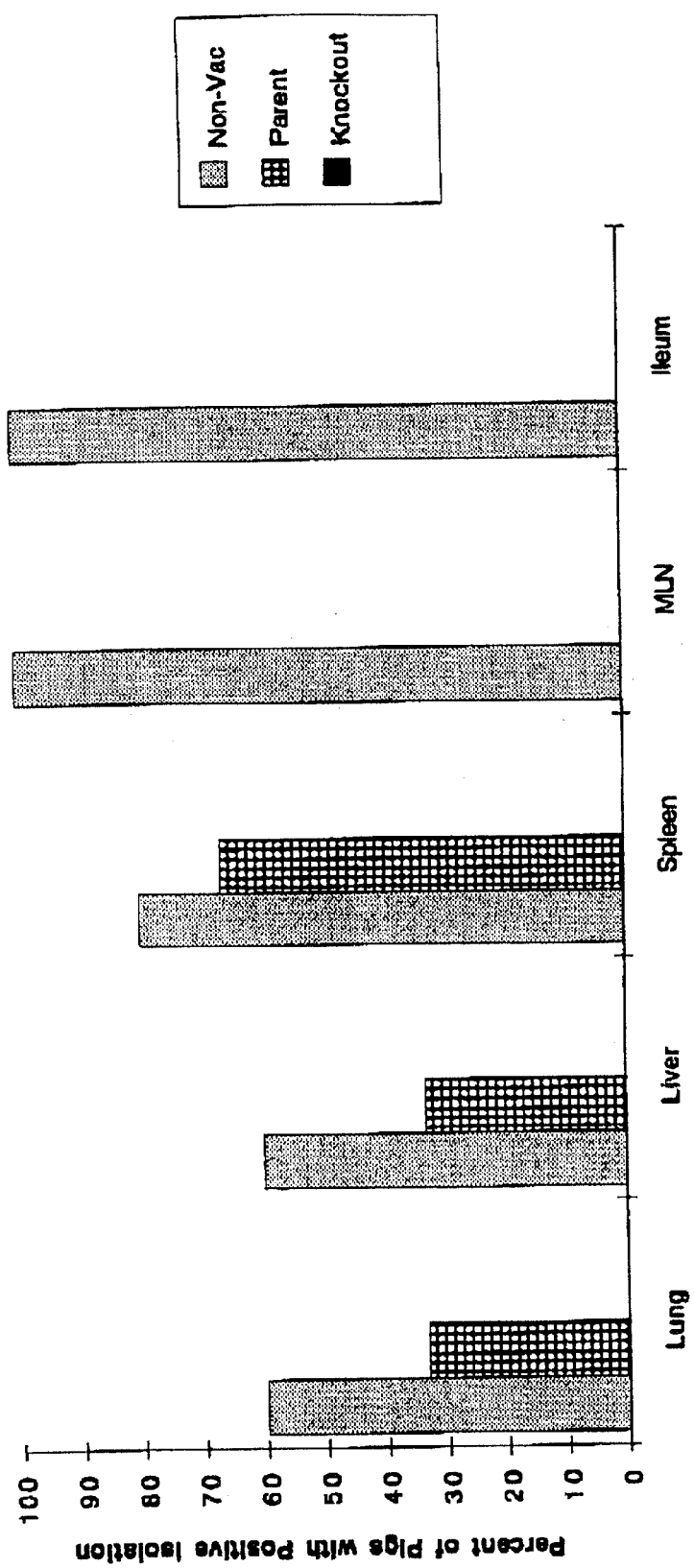
Figure 3:
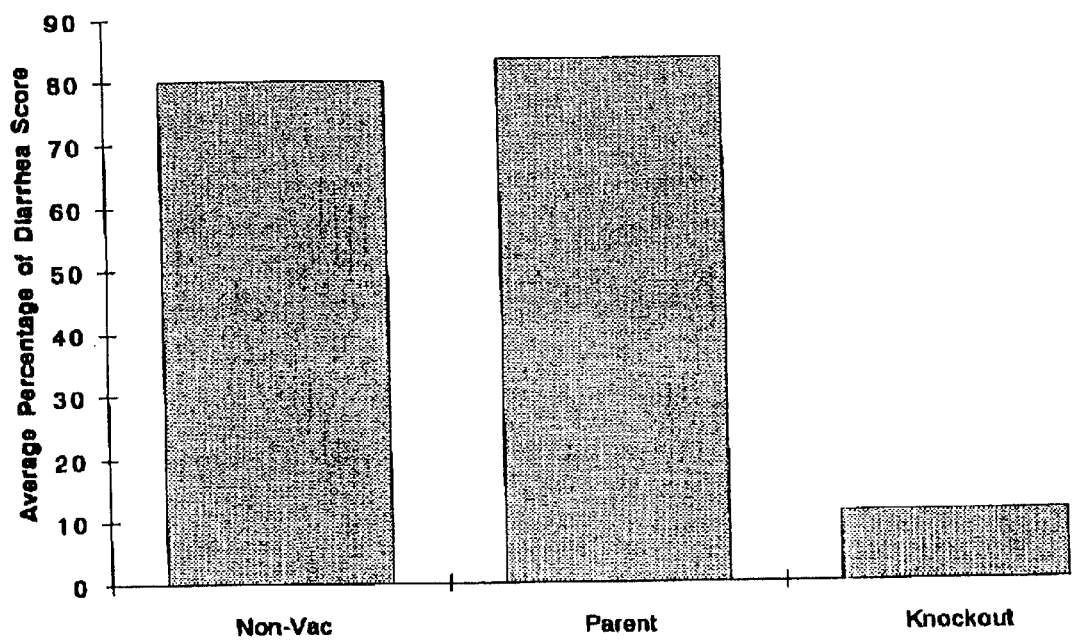
Figure 4:
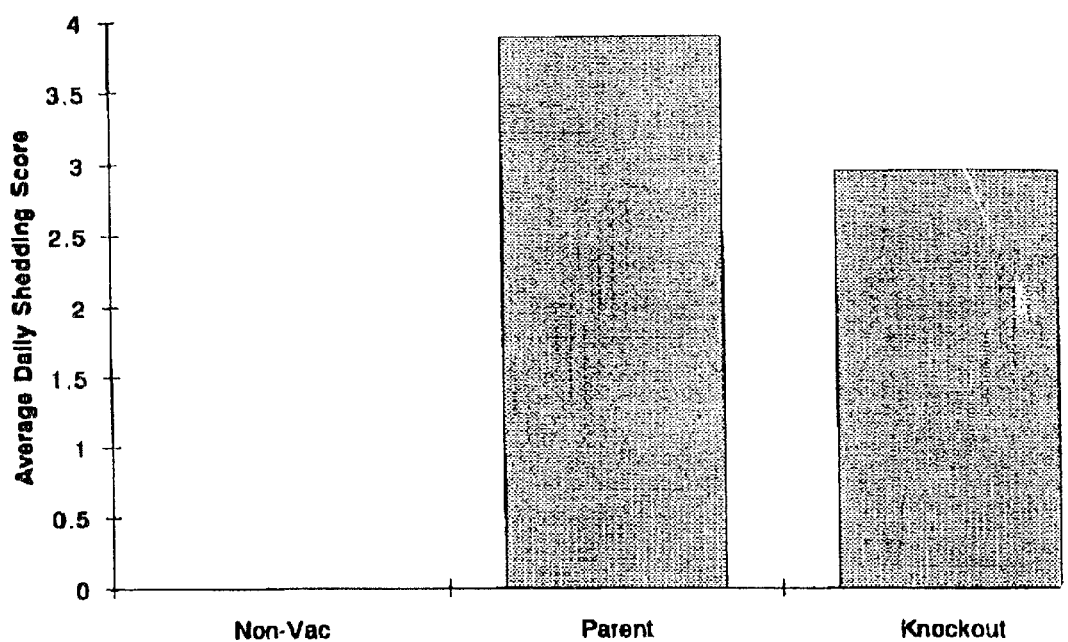
Figure 5:
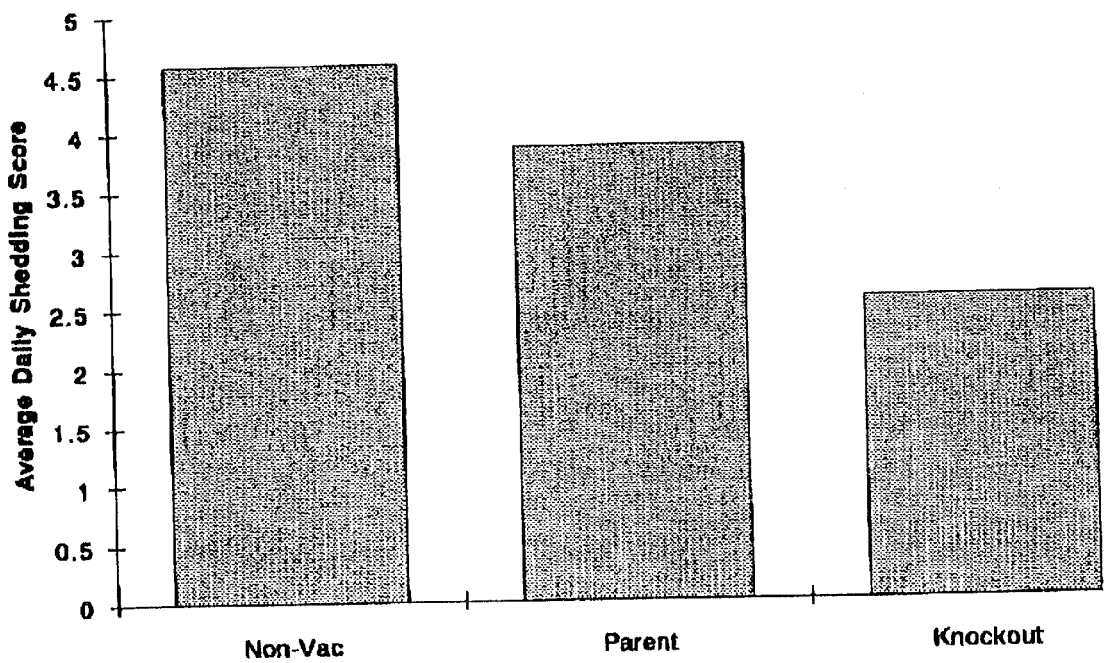

The present invention relates to live attenuated bacteria for use in a medicament, to vaccines based upon such bacteria useful for the prevention of microbial pathogenesis, to live attenuated bacteria carrying a heterologous gene and to methods for the preparation of such vaccines and bacteria.

BACKGROUND OF THE INVENTION

The means by which a warm blooded animal overcomes microbial pathogenesis is a complex process. Immunity to microbial pathogenesis is one means by which a warm blooded animal avoids pathogenesis, or suffers a less intense pathogenic state. Incomplete immunity to a given pathogen results in morbidity and mortality in a population exposed to a pathogen. It is generally agreed that vaccines based on live but attenuated micro-organisms (live attenuated vaccines) induce a highly effective type of immune response. Such vaccines have the advantage that, once the animal host has been vaccinated, entry of the microbial pathogen into the host induces an accelerated recall of earlier, cell-mediated or humoral immunity which is able to control the further growth of the organism before the infection can assume clinically significant proportions. Vaccines based on a killed pathogen (killed vaccine) are generally conceded to be unable to achieve this type of response. However, vaccines that contain a live pathogen present, depending on the level of attenuation, the danger that the vaccinated host upon vaccination may contract the disease against which protection is being sought. Therefore, it would be desirable to have a vaccine that possesses the immunising attributes of a live micro-organism but that is not capable of causing undesirable side effects upon vaccination.

The general approach for attenuating bacteria is the removal of one or more virulence factors. In most cases however, virulence factors also play a role in inducing immunity. In those cases, deletion of virulence factors unavoidably impairs the immunogenic capacities of the bacterium. This is of course an unwanted situation. A live vaccine should preferably retain the antigenic complement of the wild-type strain. Moreover, the live vaccine should be sufficiently a-virulent to avoid unacceptable pathological effects, but on the other hand it must cause a sufficient level of immunity in the host. Finally, the live attenuated vaccine strain should preferably have substantially no probability for reverting to a virulent wild type strain.

SUMMARY OF THE INVENTION

It was now surprisingly found that a gene encoding a protein known to play a role in the central carbohydrate metabolism in many bacterial genera can be deleted, causing attenuated behaviour in vivo without impairing the viability of such bacteria in vivo. Bacteria from which this gene is deleted do unexpectedly show an attenuated character. Moreover, since the encoded protein plays no role in the induction of immunity, the antigenic load of bacteria from which this gene is deleted, is identical to that of the wild-type. Therefore, such bacteria could unexpectedly be advantageously used in the field of preparation of medicaments, more specifically for the preparation of live attenuated vaccines. The gene that according to the present invention can be deleted and leads to an attenuated in vivo behaviour of the deletion mutants is a gene formerly known as the fruR gene, currently however called the cra gene. It was known that mutants lacking this gene could be grown in vitro, but only if the deficiencies due to lack of Cra activity are compensated for in the growth medium. This means that nutrients on which the Cra-deficient mutant can grow must be present in the growth medium. Generally spoken, pathogenic bacteria are self-supporting in the sense that they adapt their metabolism to the nutrients that are available. The cra gene plays such an adaptive role in many main metabolic pathways (see below). Mutants from which the cra gene has been deleted can however grow perfectly well on glucose and many other sugars as carbon source. In the host animal, such sugars are available and therefore one would not expect the cra gene to be functional under in vivo conditions. And thus, one would not expect Cra-negative mutants to show attenuated characteristics in the host. That explains why, although such mutants were known in the art, they have never been suggested to be potential live attenuated vaccine candidates.

DETAILED DESCRIPTION OF THE INVENTION

One embodiment of the invention relates to live attenuated bacteria that are no longer capable to express a functional Cra protein as a result of a mutation in the cra gene, for use in a vaccine.

The gene product, (formerly known as FruR; the Fructose Repressor Protein), now also known as Cra (the Catabolite Repressor/Activator Protein), is a regulatory protein in many main pathways of the carbohydrate metabolism.

The cra-gene product Cra regulates the central carbon metabolism. More specifically, Cra positively regulates transcription of genes encoding biosynthetic and oxidative enzymes (e.g. key enzymes in the TCA cycle, the glyoxalate shunt, the gluconeogenic pathway and electron transport) by binding upstream of the promoters of these genes and negatively regulates transcription of genes encoding glycolytic enzymes (e.g. key enzymes in the Embden-Meyerhof and Entner-Doudoroff pathways). Due to its key position in carbohydrate metabolism, the cra gene and its gene product Cra are widespread in the bacterial realm. The Cra protein is a highly conserved protein. It can be found in e.g. *Escherichia coli*, in *Salmonella enterica* species, such as serotype Typhimurium, Enteritidis and Dublin, in Actinobacillus species such as *A. pleuropneumoniae*, in Haemophilus species such as *H. paragallinarum*, in *Aeromonas salmonicidae*, in Pasteurella species such as *P. piscida* and *P. multocida*, in Streptococcus species such as *S. equi* and *S. suis* and in Yersinia species such as *Y. pestis*.

The gene itself and its complete nucleotide sequence in Salmonella and Escherichia have been elucidated already in 1991 by Jahreis, K. et al. (Mol. Gen. Genet. 226: 332–336 (1991)). Jahreis showed that the Cra protein in *Salmonella enterica*, serotype Typhimurium and *Escherichia coli* differed only in 4 positions, of which two were merely conservative exchanges. This is of course in line with what could be expected for a protein playing a role in so many universal pathways in the bacterial carbohydrate metabolism, especially where *E. coli* and Salmonella diverged not that far during evolution. The mechanism of binding of the Cra protein has been at least partially elucidated by Ramseier, T. M. et al. (J. Mol. Biol. 234:28–44 (1993)). The role and function of the Cra protein (the Catabolite Repressor/Activator Protein) have been regularly described in the literature, e.g. in a recent mini-review by Saier, M. H. and Ramseier, T. M. (Journ. Bacteriol. 178: 3411–3417 (1996)).

Such a mutation can be an insertion, a deletion, a substitution or a combination thereof, provided that the mutation leads to the failure to express a functional Cra protein. A functional Cra protein is understood to be a protein having the regulating characteristics of the wild-type protein. Therefore, a Cra protein that is defective in at least one of its functions is considered to be a non-functional Cra protein.

Live attenuated bacteria for use according to the invention can be obtained in several ways. One possible way of obtaining such bacteria is by means of classical methods such as the treatment of wild-type bacteria having the cra gene with mutagenic agents such as base analogues, treatment with ultraviolet light or temperature treatment. Strains that do not produce a functional Cra protein can easily be picked up. They grow on minimal medium exclusively in the presence of glucose and other sugars as carbon sources (which differentiates them from cya and crp mutants) but they are not able to grow with gluconeogenic substrates as sole carbon source. (Chin et al., J. Bacteriol. 169: 897–899 (1987)) They can therefore very easily be selected in vitro. The nature of the mutation caused by classical mutation techniques is unknown. This may be a point mutation which may, although this is unlikely to happen, eventually revert to wild-type. In order to avoid this small risk, transposon mutagenesis would be a good alternative. Mutagenesis by transposon mutagenesis, is also a mutagenesis-technique well-known in the art. This is a mutation accomplished at a localised site in the chromosome. Transposon-insertions can not be targeted to a specific gene. It is however very easy to pick up cra-mutants since they do not grow in vitro without nutrient compensation for lack of Cra activity. Therefore, they can easily be selected from a pool of randomly transposon-mutated bacteria. A possibility to introduce a mutation at a predetermined site, rather deliberately than randomly, is offered by recombinant DNA-technology. Such a mutation may be an insertion, a deletion, a replacement of one nucleotide by another one or a combination thereof, with the only proviso that the mutated gene no longer encodes functional Cra. Such a mutation can e.g. be made by deletion of a number of nucleic acids. Even very small deletions such a stretches of 10 nucleic acids can already render Cra non-functional. Even the deletion of one single nucleic acid may already lead to a non-functional Cra, since as a result of such a mutation, the other nucleic acids are no longer in the correct reading frame. Each deletion of insertion of a number of nucleic acids indivisible by three causes such a frame shift. More preferably, a longer stretch is removed e.g. 100 nucleic acids. Even more preferably, the whole cra gene is deleted. It can easily be seen, that especially mutations introducing a stop-codon in the open reading frame, or mutations causing a frame-shift in the open reading frame are very suitable to obtain a strain which no longer encodes functional Cra.

All techniques for the construction of Cra-negative mutants are well-known standard techniques. They relate to cloning of the Cra-gene, modification of the gene sequence by site-directed mutagenesis, restriction enzyme digestion followed by re-ligation or PCR-approaches and to subsequent replacement of the wild type cra gene with the mutant gene (allelic exchange or allelic replacement). Standard recombinant DNA techniques such as cloning the cra gene in a plasmid, digestion of the gene with a restriction enzyme, followed by endonuclease treatment, re-ligation and homologous recombination in the host strain, are all known in the art and described i.a. in Maniatis/Sambrook (Sambrook, J. et al. Molecular cloning: a laboratory manual. ISBN 0-87969-309-6). Site-directed mutations can e.g. be made by means of in vitro site directed mutagenesis using the Transformer® kit sold by Clontech. PCR-techniques are extensively described in (Dieffenbach & Dreksler; PCR primers, a laboratory manual. ISBN 0-87969-447-3 and ISBN 0-87969447-5).

The cra gene comprises not only the coding sequence encoding the Cra protein, but also regulatory sequences such as the promoter. The gene also comprises sites essential for correct translation of the Cra mRNA, such as the ribosome binding site. Therefore, not only mutations in the coding regions but also mutations in those sequences essential for correct transcription and translation are considered to fall within the scope of the invention.

In a preferred embodiment, the invention relates to live attenuated bacteria of the genera Escherichia, Salmonella, Actinobacillus, Haemophilus, Aeromonas, Pasteurella, Streptococcus and Yersinia for use in a vaccine.

In a more preferred form of the invention, the live attenuated bacterium according to the invention is selected from the group consisting of *S. enterica* serotype Typhimurium, Enteritidis, Choleraesuis, Dublin, Typhi, Gallinarum, Abortusovi, Abortus-equi, Pullorum, *E. coli* or *Y. pestis*. These bacterial genera comprise a large number of species that are pathogenic to both humans and a variety of different animals.

In an even more preferred form thereof, the live attenuated bacterium according to the invention is *S. enterica, E. coli* or *Y. pestis*.

In a still even more preferred form, this embodiment relates to live attenuated bacteria according to the invention in which the mutation in the Cra gene has been made by recombinant DNA technology.

Well-defined and deliberately made mutations involving the deletion of fragments of the cra gene or even the whole gene or the insertion of heterologous DNA-fragments or both, have the advantage, in comparison to classically induced mutations, that they will not revert to the wild-type situation. Thus, in an even more preferred form, this embodiment of the invention refers to live attenuated bacteria in which the cra gene comprises an insertion and/or a deletion.

Given the large amount of vaccines given nowadays to both pets and farm animals, it is clear that combined administration of several vaccines would be desirable, if only for reasons of decreased vaccination costs. It is therefore very attractive to use live attenuated bacteria as a recombinant carrier for heterologous genes, encoding antigens selected from other pathogenic micro-organisms or viruses. Administration of such a recombinant carrier has the advantage that immunity is induced against two or more diseases at the same time. The live attenuated bacteria for use in a vaccine, according to the present invention provide very suitable carriers for heterologous genes, since the gene encoding the Cra protein can be used as an insertion site for such heterologous genes. The use of the cra gene as an insertion site has the advantage that at the same time the cra gene is inactivated and the newly introduced heterologous gene can be expressed (in concert with the homologous bacterial genes). The construction of such recombinant carriers can be done routinely, using standard molecular biology techniques such as allelic exchange. Therefore, another embodiment of the invention relates to live attenuated recombinant bacteria, preferably of the genera Escherichia, Salmonella, Actinobacillus, Haemophilus, Aeromonas, Pasteurella, Streptococcus and Yersinia that do not produce a functional Cra protein, and in which a heterologous gene is inserted. Such a heterologous gene can, as mentioned above, e.g. be a gene encoding an antigen selected from other pathogenic micro-organisms or viruses. Such genes can e.g. be derived from pathogenic herpes viruses (e.g. the genes encoding the structural proteins of herpes viruses), retro viruses (e.g. the gp160 envelope protein), adenoviruses and the like. Also a heterologous gene can be obtained from pathogenic bacteria. As an example, genes encoding bacterial toxins such as *Actinobacillus pleuropneumoniae* toxins, Clostridium toxins, outer membrane proteins and the like are very suitable bacterial heterologous genes. Another possibility is to insert a gene encoding a protein involved in triggering the immune system, such as an interleukin or an interferon, or another gene involved in immune-regulation.

Insertion of the heterologous gene in the cra gene is advantageous, since there is no need to find an insertion site for the heterologous gene, and at the same time the cra gene is knocked out. Thus, in a preferred form of this embodiment the heterologous gene is inserted in the cra gene. The heterologous gene can be inserted somewhere in the cra gene or it can be inserted at the site of the cra gene while this gene has been partially or completely deleted.

Because of their unexpected attenuated but immunogenic character in vivo, the bacteria for use in a vaccine, according to the invention are very suitable as a basis for live attenuated vaccines. Thus, still another embodiment of the invention relates to live attenuated vaccines for the protection of animals and humans against infection with a bacterium of which the wild type form comprises a cra gene. Such vaccines comprise an immunogenically effective amount of a live attenuated bacterium for use in a vaccine, according to the invention or a live recombinant carrier bacterium according to the invention, and a pharmaceutically acceptable carrier.

Preferably, the vaccine comprises a live attenuated bacterium according to the invention, selected from the group of Escherichia, Salmonella, Actinobacillus, Haemophilus, Aeromonas, Pasteurella, Streptococcus and Yersinia. Immunogenically effective means that the amount of live attenuated bacteria administered at vaccination is sufficient to induce in the host an effective immune response against virulent forms of the bacterium.

In addition to an immunogenically effective amount of the live attenuated bacterium described above, a vaccine according to the present invention also contains a pharmaceutically acceptable carrier. Such a carrier may be as simple as water, but it may e.g. also comprise culture fluid in which the bacteria were cultured. Another suitable carrier is e.g. a solution of physiological salt concentration.

The useful dosage to be administered will vary depending on the age, weight and animal vaccinated, the mode of administration and the type of pathogen against which vaccination is sought.

The vaccine may comprise any dose of bacteria, sufficient to evoke an immune response. Doses ranging between $10^3$ and $10^{10}$ bacteria are e.g. very suitable doses.

Optionally, one or more compounds having adjuvant activity may be added to the vaccine. Adjuvants are non-specific stimulators of the immune system. They enhance the immune response of the host to the vaccine. Examples of adjuvants known in the art are Freunds Complete and Incomplete adjuvant, vitamin E, non-ionic block polymers, muramyldipeptides, ISCOMs (immune stimulating complexes, cf. for instance European Patent EP 109942), Saponins, mineral oil, vegetable oil, and Carbopol. Adjuvants, specially suitable for mucosal application are e.g. the *E. coli* heat-labile toxin (LT) or Cholera toxin (CT). Other suitable adjuvants are for example aluminium hydroxide, aluminium phosphate or aluminium oxide, oil-emulsions (e.g. of Bayol F® or Marcol 52®, saponins or vitamin-E solubilisate.

Therefore, in a preferred form, the vaccines according to the present invention comprise an adjuvant.

Other examples of pharmaceutically acceptable carriers or diluents useful in the present invention include stabilisers such as SPGA, carbohydrates (e.g. sorbitol, mannitol, starch, sucrose, glucose, dextran), proteins such as albumin or casein, protein containing agents such as bovine serum or skimmed milk and buffers (e.g. phosphate buffer). Especially when such stabilisers are added to the vaccine, the vaccine is very suitable for freeze-drying. Therefore, in a more preferred form, the vaccine is in a freeze-dried form.

For administration to animals or humans, the vaccine according to the present invention can be given inter alia intranasally, intradermally, subcutaneously, orally, by aerosol or intramuscularly. For application to poultry, wing web and eye-drop administration are very suitable.

Still another embodiment relates to the use of a bacterium for use in a vaccine or a recombinant bacterium according to the invention for the manufacture of a vaccine for the protection of animals and humans against infection with a wild type bacterium or the pathogenic effects of infection.

Still another embodiment of the invention relates to methods for the preparation of a vaccine according to the invention. Such methods comprise the admixing of a live attenuated bacterium according to the invention or a live recombinant carder bacterium according to the invention, and a pharmaceutically acceptable carrier.

EXAMPLES

Example 1

Identification, Cloning and Sequencing of the Mutated Gene in *S. typhimurium* SR-11 Fad⁻

The transposon-mutated gene of the mutant *S. typhimurium* SR-11 Fad⁻ has been identified, cloned and sequenced. The nucleotide sequence of the mutant gene that renders the disclosed SR-11 Fad⁻ a-virulent is set forth in Sequence ID NO:1. Sequence ID NO:2 sets forth the amino acid sequence of the protein molecule that the nucleotide sequence of Sequence ID NO:1 encodes. It was now determined that *S. typhimurium* SR-11 Fad$^-$ is mutant in the cra gene. The point of the transposon insertion has been found to be located within the range of about 45 base pairs from the 3' end of the cra translational stop codon. A 4.5 kb Pstl fragment containing the 1.5 kb Tn 10 d Cam insertion flanked by a 1.9 kb *S. typhimurium* SR-11 DNA fragment on the one end and a 1.1 kb *S. typhimurium* SR-11 DNA fragment on the other end was inserted in the Pstl site of pBluescript II SK (+). The resulting plasmid, pJHA7, was put into *E. Coli* HB101 by electroporation. The regions flanking the Tn10 d Cam insertion were sequenced using the Sanger Dideoxy Thermal Cycling Method. The nucleotide sequences immediately flanking each side of the Tn 10 d Cam insertion were found to be 100% homologous to the *S. typhimurium* cra (fruR) gene and the point of the insertion was found to be 45 nucleotides from the 3' end of the cra translational stop codon. This suggested that *S. typhimurium* SR-11 Fad$^-$ is a cra mutant. In contrast to SR-11, SR-11 Fad$^-$ failed to grow on M9 minimal agar plates containing citrate, oleate, pyruvate, acetate, succinate and fumarate. The *S. typhimurium* SR-11 wild type cra (fruR) was amplified by PCR and was inserted into the PstI site in the ampicillin resistance gene of pBR322. The resulting plasmid, pJHA8, returned the ability of *S. typhimurium* SR-11 Fad⁻ to grow as well as their wild type parents utilising each of the aforementioned compounds as carbon sources. These experiments establish that *S. typhimurium* SR-11⁻is a cra (fruR) mutant.

SR-11 Fad⁻ was constructed by bacteriophage P22 HT105 int transduction of chloramphenicol resistance from a mini-transposon mutant of LT-2 into SR-11. Although unlikely, it was therefore possible that avirulence of SR-Fad⁻ was due to loss of some SR-11 DNA upon transduction, e.g. loss of a pathogenicity island, rather than due to a defective cra gene. Therefore, as described immediately below, a strain identical to SR-11, hereinafter SR-11 Cra$^{mod}$ AX-2, except that it contains the same mutation in the cra gene that is present in SR-Fad⁻, was constructed by allelic exchange.

The 4.3 kb PstI SR-11 Fad⁻ DNA fragment that contains the SR-11 Fad⁻ mutant cra gene (chloramphenicol resistance gene in cra) was inserted into the PstI site of pLD55, a suicide vector that contains both an ampicillin resistance gene and a tetracycline resistance gene (tetAR). This was named pMJN10. pMJN10 was put into *E. coli* S17-1 λpir by electroporation. Following mating of *E. coli* S17-1 λpir (pMJN10) with SR-11, several ampicillin, tetracycline, and chloramphenicol SR-11 transconjugants were tested for the ability to utilise oleate, citrate, actetate, pyruvate, succinate, and fumarate as sole carbon sources. All were able to do so as would be expected if pMJN10 had integrated into the chromosome by a single crossover using homologous sequences, i.e. as if both the mutant and wild type cra alleles were present in the chromosome. Five of these "integrants" were tested for the presence of pMJN10 as a free plasmid and none had it, further suggesting that the plasmid had inserted in the SR-11 chromosome. Each of the five integrants were streaked on a Luria agar plate containing chloramphenicol. In this instance, cells in which a second crossover takes place survive only if the cra allele left in the chromosome is the mutant allele containing the chloramphenicol resistance gene. Samples of the streaked integrants were then streaked on tetracycline sensitive selection agar (TSS agar). TSS agar contains fumaric acid and tetracycline sensitive cells, i.e. cells that have lost the suicide plasmid come up as very large colonies relative to the tetracycline resistance cells that still have the plasmid in the chromosome. A total of 34 large colonies were tested for resistance to chloramphenicol, sensitivity to ampicillin and tetracycline and for the ability to utilise oleate, acetate, pyruvate, citrate, succinate, and fumarate as sole carbon sources. Of the 34 isolates, six were resistance to chloramphenicol, sensitive to ampicillin and tetracycline, and were unable to utilise the aforementioned compounds as sole carbon sources. One of the isolates, designated SR-11 Cra$^{mod}$ AX-2 (AX meaning allelic exchange), was transformed with either pBR322 or pJHA8 (pJHA8 containing the wild type cra gene) and both strains were tested for the ability to utilise glucose, glycerol, oleate, acetate, pyruvate, citrate, succinate, and fumarate as sole carbon sources. In contrast to SR-11 Cra$^{mod}$ AX-2 (pBR322), SR-11 Cra$^{mod}$ AX-2 (pJHA8) was able to utilise the aforementioned compounds as sole carbon sources, suggesting that SR-11 Cra$^{mod}$ AX-2 is a cra mutant. Both strains, as expected, were able to use glucose and glycerol as sole carbon sources. To determine whether a functional cra(fruR) gene renders *S. typhimurium* SR-11 virulent the following experiments were performed.

Four BALB/c mice were infected perorally with SR-11 (2.1×108 cfu/mouse) and 5 mice with SR-11 Cra$^{mod}$ AX-2 (2.8×10⁸ cfu/mouse). By day 8 post infection, all 4 SR-11 infected mice had died, whereas all 5 mice infected with SR-11 Cra$^{mod}$ AX-2 remained healthy and active (Table 1). Since SR-11 Cra$^{mod}$ AX-2 is identical to SR-11 with the exception of the same mutation in cra that is present in SR-11 Cra$^{mod}$ the possibility is eliminated that something anomalous happened during construction of SR-11 Cra$^{mod}$ by transduction from the LT-2 strain, unrelated to cra, that could account for its loss of virulence.

It was also still possible that insertion of the chloramphenicol resistance cassette into the cra gene resulted in a polar effect on downstream genes and therefore that the attenuation of SR-11 Fad⁻ was not due to a defective cra gene. Therefore, the SR-11 Cra$^{mod}$ was complemented with pJHA8, which only contains the wild type cra gene, with the intent of determining whether SR-11 Cra$^{mod}$ (pJHA8) regained virulence. As a control, SR-11 Cra$^{mod}$ was complemented with pBR322, the vector used in constructing pJHA8. Four BALB/c mice were infected perorally with 3.1×10⁸ cfu/mouse of SR-11 Cra$^{mod}$ (pBR322) and 4 mice with 4.3×10⁸ cfu/mouse of SR-11 Fad⁻ (pJHA8). By day 9 post infection 3 of the 4 mice infected with SR-11 Cra$^{mod}$ (pJHA8) had died whereas the 4 mice infected with SR-11 Cra$^{mod}$ (pBR322) remained healthy and active (Table 1). The livers and spleens of all mice that died had greater than 10⁸ cfu per organ of SR-11 Fad⁻ (pJHA8). This result rules out the possibility that inactivation of the cra gene with a chloramphenicol cassette causes a downstream effect that results in avirulence and proves that a functional cra gene is required for SR-11 virulence.

TABLE 1

| *S. typhimurium* strain | Number infected[a] | Number Surviving |
|---|---|---|
| SR-11 | 4 | 0 |
| SR-11 Cra$^{mod}$ Ax-2 | 5 | 5 |
| SR-11 Cra$^{mod}$ (pBR322) | 4 | 4 |
| SR-11 Cra$^{mod}$ (pJHAB) | 4 | 1 |

[a]Mice were infected perorally with between 2.0 × 10⁸ cfu/mouse and 5.0 × 10⁸ cfu/mouse, depending on the strain. All mice that died did so by day 9 post infection. All mice that survived recovered completely.

Detection of the cra Gene in Various Bacterial Genera

Four *S. typhimurium* strains, and one strain each of *S. enteritidis*, *S. gallinarum*, *S. dublin*, and *S. choleraesuis* were tested for the cra gene by Southern hybridisation. In all cases the cra gene was found on the same size 4.3 kb PstI DNA fragment as SR-11. Six different pathogenic *E. coli* strains were also tested and all had the cra gene, although the gene was present in three different size PstI fragments among the six strains. In addition, an *Aeromonas salmonicidae* strain and strains of the bacterial genera Actinobacillus, Haemophilus, Pasteurella, Streptococcus and Yersinia were tested and all showed the presence of a cra gene.

The presence of the cra gene in the bacteria mentioned above was demonstrated as follows: Genomic DNA of these strains was digested with 20 units of PstI (Promega) at 37° C. overnight. Gel electrophoresis (0.7% agarose, 1×TAE) was used to separate the various size PstI DNA fragments. The separated DNA was transferred under alkaline conditions to positively charged nylon for 3 hours using the S&S Turboblotter system (Schleicher and Schuell). The membrane was baked for 30 minutes at 90° C. to bind the DNA to the membrane. Subsequently, a 700 basepair fragment of the cra gene of Salmonella typhimurium was DIG labelled and used to probe the membrane. The membrane was prehybridised (in a roller bottle hybridisation oven) at 62° C. for 24 hours in hybridisation buffer containing 5×SSC, 0.1% N-lauroylsarcosine, 0.02% SDS, 1.5% blocking reagent (from DIG Detection Starter Kit II with CSPD, Boehringer Mannheim). Labelled probe was denatured and added to fresh hybridisation buffer and the blot was incubated at 62° C. for 16–20 hours. Blots were washed twice with 2×SSC, 0.1% SDS at 62–65° C. for 5 min. Blots were then washed twice with 0.1% SDS, 0.5×SSC at 60° C. for 15 min. The blots were developed as recommended with the following modification: 2% blocking reagent was used in the blocking solution (1% is normally used), blots were blocked for an hour (30 min. is the normal blocking time) and a lower concentration of the antibody (70% of the concentration normally used) was used for the detection of the DIG-labelled probe. These changes were recommended by the manufacturer for lower background signal.

Example 2

Vaccination of Chickens with Cra-negative
Salmonella typhimurium Strain SR11 Cra$^{mod}$ Efficacy of vaccination. Growth conditions for the Salmonella strains were comparable to those described in Example 2. In one experiment two groups of 20 broilers (at 3 days of age) were vaccinated orally with 6×10$^7$ CFU Salmonella t. SR11 Cra$^{mod}$ in PBS. One group was boosted after 11 days with 8.3×10$^7$ CFU of the same strain. After 18 days, both groups were challenged subcutaneously, intramuscularly and orally with 1.9×10$^9$ bacteria of a virulent wild type strain. Table 2 gives the results.

TABLE 2

|  | SR11 Cra$^{mod}$ | SR11 Cra$^{mod}$ | Control |
| --- | --- | --- | --- |
| Vacc. Dose day 1 | 6.0 × 10$^7$ | 6.0 × 10$^7$ | — |
| Vacc. Dose day 11 | — | 8.3 × 10$^7$ | — |
| Chall. Dose day 18 | 1.9 × 10$^9$ | 1.9 × 10$^9$ | 1.9 × 10$^9$ |
| Mortality (%) | 15 | 10 | 100 |

Combined vaccination safety and efficacy experiment. In a second experiment both the efficacy of the vaccine and the safety of the vaccine were determined. The safety of the vaccine was determined on the basis of growth retardation. One group of 15 broilers was vaccinated orally with 2.7×10$^8$ CFU Salmonella t. SR11 Craze in culture medium. Another group of 15 broilers was vaccinated orally with 1.3×10$^8$ CFU of the same strain in PBS. After 18 days, both groups were challenged subcutaneously, intramuscularly and orally with 6.5×10$^8$ bacteria of a virulent wild type strain. Table 3 gives the results.

TABLE 3

|  | SR11 Cra$^{mod}$ (i) | SR11 Cra$^{mod}$ (ii) | Control |
| --- | --- | --- | --- |
| Vacc. Dose day 1 | 2.7 × 10$^8$ | 1.3 × 10$^8$ | — |
| Weight day 7 | 178 | ND | 185 |
| Weight day 18 | 733 | 722 | 749 |
| Chall. Dose Day 18 | 6.5 × 10$^8$ | 6.5 × 10$^8$ | 6.5 × 10$^8$ |
| Mortality (%) | 0 | 13 | 100 | i = culture medium,
ii = PBS

Results: Both experiments show, that a very high level of protection is obtained with a Cra-negative Salmonella typhimurium strain, in spite of the high challenge dose given. In addition, no significant growth retardation as a result of vaccination is seen. Therefore it can be concluded that Cra-negative Salmonella typhimurium strains are very suitable in live attenuated vaccines for the protection of poultry against infection with a wild type bacterium.

Example 3

Introduction

A pig challenge study was done to determine the safety of *Salmonella choleraesuis* Cra negative knockout (KO) strains 34682 and 35276 compared to cra positive parent strains 34682 and 35276. These knockout mutants were made using the plasmids and methods identical to those described above for the construction of $Cra^{mod}$ AX-2.

1. Pig Safety Testing

A. Animals and Housing

Twenty (20) 5–6 week old pigs that had never been vaccinated for Salmonella were purchased from a farm with no history of Salmonella. The pigs were divided into four groups of 5 pigs. Throughout the study, the pigs were housed in 4 isolation rooms.

B. Challenge

Five pigs in each group were challenged at 5–6 weeks of age. The pigs were challenged intranasally (0.5 ml/nare) and orally (1.0 ml culture+4.0 ml bacterial diluent). The challenge culture was approximately $9.0\times10^8$ CFU/ml. Following challenge, the pigs were observed daily for clinical signs typical of Salmonella infection including weight loss, diarrhoea, and elevated rectal temperature.

C. Sacrifice

Seven days post-challenge, the pigs were euthanized. The pigs were necropsied and the lungs, liver, spleen, mesenteric lymph nodes (MLN), and ileum were cultured for growth of *S. choleraesuis.*

D. Weight Gain

The average daily gain (ADG) was calculated by subtracting the beginning weight from the end weight and dividing by the number of days from challenge to sacrifice. Group ADG is the mean of the individual pig ADG.

2. Mice Safety Testing

A mouse study was done to determine the LD50 of various *S. choleraesuis* strains; cra positive parent strains 34682 and 35276, and cra negative knockout (KO) strains 34682 and 35276.

A. Animals

Two hundred (200) 16–20 grams CF-1 Sasco mice were divided into 20 groups of 10 mice each for the mouse safety testing. Throughout the study the mice were housed in the same room, but in different tubs.

B. Challenge

Each strain had 5 subgroups containing 10 mice each. These subgroups were challenged with 0.25 ml intraperitoneally (IP) using 5 different dilutions of the strain ($10^{-3}$–$10^{-7}$). Frozen seeds of each of the four strains were diluted $10^{-3}$–$10^{-7}$. Each of these dilutions were injected intraperitoneally (0.25 ml) into 10 mice.

Results

I. Pig Safety Testing

A. Weight Gain

The weight gain of the pigs is shown in FIG. 1. These data clearly show differences between pigs challenged with KO strains and pigs challenged with parent strains. The data also reflect the overall health differences of the animals. Both groups of pigs challenged with the parent strains lost weight from the time of challenge until sacrifice; whereas the pigs challenged with the KO strains gained approximately 0.75 kilograms per day.

II. Mouse Safety Testing

A. Death

The results of the mouse study are shown in table 4 below. The right column shows the LDSO in CFUs of the various strains. The knockout strains clearly show a high level of attenuation.

TABLE 4

| Strain | $LD_{50}$ cfu |
|---|---|
| 35276 Parent | <7.7 cfu |
| 35276 Knockout | 1.5E + 04 cfu |
| 34682 Parent | 12.5 cfu |
| 34682 Knockout | >9.0E + 04 cfu |

Conclusion

From the pig safety test it shows that Cra knockout (KO) strains give a significantly higher weight gain post challenge, when compared to the parent strains. This demonstrates the attenuated character of the Cra KO mutants. In addition to pig safety testing, mouse safety testing also showed that the Cra KO strains were attenuated: the $LD_{50}$ of the KO-mutants is dramatically higher than that of the parent strains.

Example 4

Introduction

The purpose of this Example was to evaluate the safety of the KO-34682 Cra mutant compared to its parent strain, and to determine the efficacy of Salmonella strain KO-34682 against heterologous virulent Salmonella strain 35276 challenge. In addition, efficacy of the KO-34682 Cra mutant was compared to non-vaccinated controls.

Animals and Housing

Twenty 3 week old pigs that have never been vaccinated for Salmonella were purchased from a farm with no history of Salmonella. The pigs were divided into four groups of 5 pigs and were housed in 4 separate isolation rooms.

Vaccines and Vaccinations

Pigs were vaccinated orally at 3 weeks of age with approximately $1\times10^9$ CFU/ml of *Salmonella choleraesuis* strain KO-34682, the 34682 parent, or left non-vaccinated.

Challenge

Twenty-one days following vaccination, the pigs were challenged intranasally (0.5 ml/nare) and orally (1.0 ml culture+4.0 ml bacterial diluent) with virulent *Salmonella choleraesuis* strain 35276. The 35276 challenge strain was made nalidixic acid (Nal) resistant prior to challenge so plates containing Nal could be used to differentiate the challenge strain from the vaccine strain. Following challenge, the pigs were observed daily for clinical signs typical of Salmonella infection including weight loss, diarrhoea, and elevated rectal temperatures. The duration of Salmonella shedding was evaluated by culturing the faces daily.

Nine days post-challenge, the pigs were euthanized. The pigs were necropsied and the lungs, liver, spleen, mesenteric lymph nodes (MLN), and ileum were cultured for growth of *Salmonella choleraesuis* on Hektoen enteric (HE) agar plates containing 80 ug/ml of nalidixic acid.

Diarrhoea Score

The diarrhoea score was calculated by giving one point to each pig for each day of diarrhoea post-challenge. At the end of the test, the total number of points scored during the study were divided by the number of days from challenge until sacrifice. This number was multiplied by 100 to give the percentage of days the diarrhoea was seen.

Salmonella Shedding

Fecals were taken from the pigs daily to determine the length of *Salmonella choleraesuis* shedding post-vaccination and again post-challenge. After 2 days of negative results, taking fecals was stopped. The fecals were titered on HE plates for isolation. Points were given in relation to growth seen after various dilutions of the samples. Points were assigned as follows:

| | |
|---|---|
| $10^{-1}$ | 1 pt |
| $10^{-2}$ | 2 pts |
| $10^{-3}$ | 3 pts |
| $10^{-4}$ | 4 pts |
| $10^{-5}$ | 5 pts |

Weight Gain

The average daily gain (ADG) was calculated by subtracting the beginning weight from the end weight and dividing by the number of days from challenge to sacrifice. Group ADG is the mean of the individual pig ADG.

Results

Death Post-Vaccination

Two pigs that were vaccinated with *Salmonella choleraesuis* wild type parent strain 34682 died post-vaccination. The other three pigs in this group remained alive throughout the end of the study.

Salmonella Isolation/Necropsy Score

FIG. 2 shows the *S. c.* isolation results for each organ. For all organs, groups of pigs vaccinated with the KO vaccine had no isolation from any organ compared to the parent and non-vac groups. The non-vac group had *Salmonella choleraesuis* isolated from all 5 pigs in the ileum and the MLN whereas the parent group had no isolation in either of those organs. By assigning one point to each organ *Salmonella choleraesuis* was isolated from, an isolation score was calculated for each group. The results demonstrate that the pigs vaccinated with the KO vaccine had lower scores than the pigs vaccinated with the parent strain, and were significantly lower than the non-vacs.

Diarrhoea Score

The average daily diarrhoea score is shown in FIG. 3. This figure shows a significant difference in the KO scores compared to the other three groups. The KO group clearly showed the lowest score.

Salmonella Shedding

The Salmonella shedding of the pigs following vaccination and post-challenge are shown in FIGS. 4 and 5. Following vaccination, the chart shows the parent having the highest level of shedding. In the post-challenge chart, the non-vaccinates shed *Salmonella choleraesuis* for the longest duration, thus receiving the highest score.

Weight Gain

Figure 6:
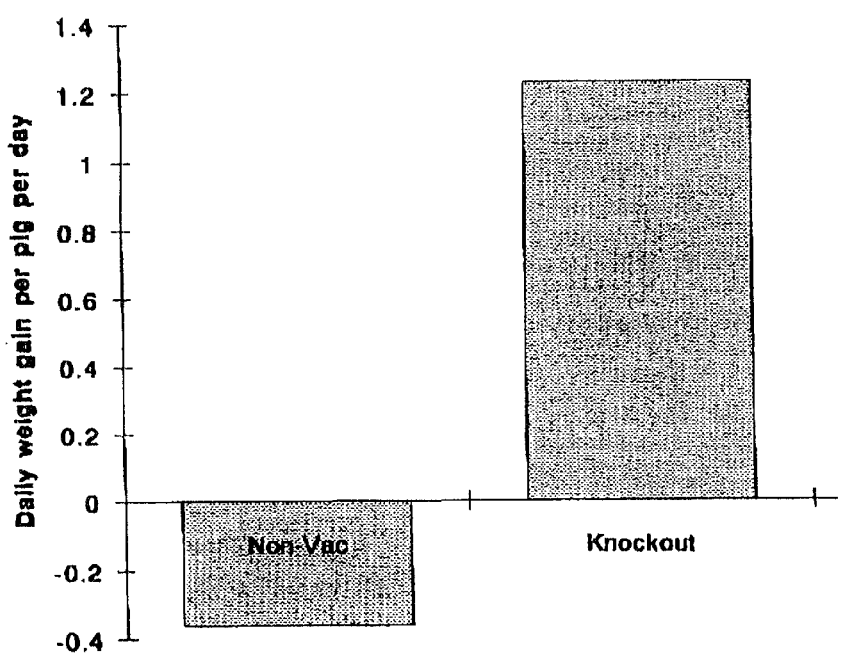

The weight gain of the pigs is shown in FIG. 6. These data clearly shows differences between the different groups. They also reflect the overall health differences between the animals. The non-vac group lost an average of 0.15 kilograms per day, whereas the KO group gained an average of 0.6 kilograms per day.

Discussion

*Salmonella choleraesuis* Knockout strain 34682 proved to be an efficacious and safe vaccine strain. Isolation of Salmonella at necropsy was completely negative for the knockout strain. The non-vaccinates scored the highest in re-isolation. Concerning average daily weight gain post challenge, the knockout strain had the highest weight gain and non-vacs had significantly less weight gain.

Conclusion

The live KO-34682 *Salmonella choleraesuis* vaccine strain is safe and efficacious.

BRIEF DESCRIPTION OF THE DRAWINGS

FIG. 1: Average daily weight gain post-challenge per pig per day in US-pounds. This weight multiplied by 0.4536 gives the weight in kilograms.

FIG. 2: Percentage of pigs from which *Salmonella choleraesuis* could be re-isolated from various tissues (MLN= mesenteric lymph node).

FIG. 3: Average percentage of diarrhoea score post-challenge.

FIG. 4: Average daily Salmonella shedding score post-vaccination.

FIG. 5: Average daily bacterial shedding score post-challenge.

FIG. 6: Average daily weight gain post-challenge per pig per day in US-pounds.

---

We claim:

1. A live attenuated vaccine for the protection of animals against infection with pathogenic Escherichia or Salmonella, said live attenuated vaccine comprising:
   from about 1×10³ to about 1×10¹⁰ of a live attenuated bacterium selected from the group consisting of Eschenrchia and Salmonella, said live attenuated bacteria incapable of expressing a functional Catabolite Repressor/Activator ("Cra") protein as a result of a mutation in the cra gene, and
   an adjuvant.

2. A live attenuated vaccine for the protection of animals against infection with pathogenic Escherichia or Salmonella, said live attenuated vaccine comprising:
   a live attenuated bacterium selected from the group consisting of Eychenchia and Salmonella, said live attenuated bacteria incapable of expressing a functional Catabolite Repressor/Activator ("Cra") protein as a result of a mutation in the cra gene,
   an adjuvant; and where said live attenuated vaccine is in a freeze-dried form.

3. A method forthe preparation of a vaccine according to claim 1, comprising admixing the live attenuated bacterim with the adjuvant.

4. A method for immunizing an animal against infection with a pathogenic bacteria, comprising administering to the animal a vaccine according to claim 1.

5. A live attenuated vaccine for the protection of animals against infection with pathogenic Escherichia or Salmonella, said live attenuated vaccine comprising:
   a live attenuated bacterium, said live attenuated bacterium selected from the group consisting of Eschefichia and Salmonella, said live attenuated bacteria carrying a heterologous gene and being incapable of epressing afunctional Catabolite Repressor/Activator ("Cra") protein as a result of a mutation in the cra gene and said live attenuated bacterium, and
   an adjuvant.

6. The live attenuated vaccine according to claim 5, which is in a freeze-dried form.

7. A method for immunizing an animal against infecton vith a pathogenic bacteria, comprising administering to the animal a vaccine according to claim 5.

8. A live attenuated vaccine for protecting a subject against infection with pathogenic Eseherichia or Salmonella, said live attenuated vaccine comprsing:

from about $1\times10^3$ to about $1\times10^{10}$ live attenuated bacterium having a deletion in the live attenuated bacterium's cra gene rendering said live attenuated bacterium unable to express a functional Catabolite Repressor/Activator ("Cra ") protein, said live attenuated bacterium selected from the group consisting of Eschenchia and Salmonella, and an adjuvant.

9. A live attenuated vacine for protecting a subject aganst infection with pathogenic Escherichia or Salmonella, said live attenuated vaccine comprising:

from about $1\times10^3$ to about $1\times10^{10}$ live attenuated bacterium having a deletion in the live attenuated bacterium's cra gene rendering said live attenuated bacterium unable to express a functional Catabolite Repressor/Activator ("Cm") protein, said live attenuated bactern selected from the group consisting of Escherichia and Salmonella; and an adjuvant selected from *E. coli* heat-labile toxin or Cholera toxin.

10. A method for the preparation of a vaccine according to claim 5, comprising admixing the live attenuated bacterium with the adjuvant.

11. The live attenuated vaccine of claim 1, wherein the adjuvant is selected from the group consisting of *E. coli* heat-labile toxin and Cholera toxin.

12. The live attenuated vaccine of claim 5, wherein the adjuvant s selected from the group consisting of *E. coli* heat-labile toxin and Cholera toxin.

13. A live attenuated vaccine for the protection of a subject against Salmonella infection, said live attenuated vaccine comprising:

alive attenuated Salmonella bacteria capable of expressing a functional Catabolite/Repressor/Activator ("Cra") protein as a result of a mutation in the cra gene, and an adjuvant, wherein said live attenuated vaccine contains sufficient live attenuated Salmonella bacteria to elicit an immune response in an animal to which it is administered.

14. The live attenuated vaccine according to claim 13, which is in a freeze-dried form.

15. The live attenuated vaccine of claim 13, wherein the live attenuated Salmonella bacteria carries a heterologous gene.

16. The live attenuated vaccine according to claim 15, which is in a freeze-dried form.

17. A method for the preparation of a vaccine according to claim 13, comprising admixing the live attenuated Salmonella bacteria with the adjuvant.

18. The method according to claim 17, wherein the live attenuated Salmonella bacteria carries a heterologous gene.

19. A method of protecting a subject against infection with Salmonella comprising administering to the subject the vaccine of claim 13.

20. A live attenuated vaccine for the protection of a subject against infection with pathogenic Escherichia or Salmonella, said live attenuated vaccine comprising:

a live attenuated bacterium having a deletion in the live attenuated bacterium's cra gene rendering said live attenuated bacterium unable to express a functional Catabolite Repressor/Activator ("Cra") protein, said live attenuated bacterium selected from the group consisting of Escherichia and Salmonella, and an adjuvant selected from *E. coli* heat-labile toxin or Cholera toxin.

21. A method of protecting a subject against infection with pathogenic Escherichia or Salmonella, said method comprising:

administering to said subject from about $1\times10^3$ to about $1\times10^{10}$ of a live attenuated bacterium selected from the group consisting of Escherchia and Salmonella, said live attenuated bacteria incapable of expressing a functional Catablilte Repressor/Activator ("Cra") protein as a result of a mutation in the cra gene.

22. A method of protecting a subject against Salmonella infection, said method comprising:

administering to said subject a sufficient amount of a live attenuated Salmonella bacteria incapable of expressing a functional Catabolite Repressor/Activator ("Cra") protein as a result of a mutation in the cra gene to elicit an immune response in said subject.

* * * * *